(12) United States Patent
Liao et al.

(10) Patent No.: US 10,781,159 B2
(45) Date of Patent: Sep. 22, 2020

(54) HYDROGENATION METHOD FOR INCREASING YIELD OF CYCLOHEXANE-1,4-DICARBOXYLIC ACID DIISOOCTYL ESTER

(71) Applicant: NAN YA PLASTICS CORPORATION, Taipei (TW)

(72) Inventors: Te-Chao Liao, Taipei (TW); Jung-Jen Chuang, Taipei (TW); Chung-Yu Chen, Taipei (TW); Chia-Ruey Tsai, Taipei (TW); Sung-Chieh Chao, Taipei (TW)

(73) Assignee: NAN YA PLASTICS CORPORATION, Taipei (TW)

( * ) Notice: Subject to any disclaimer, the term of this patent is extended or adjusted under 35 U.S.C. 154(b) by 0 days.

(21) Appl. No.: 16/656,883

(22) Filed: Oct. 18, 2019

(65) Prior Publication Data
US 2020/0172463 A1    Jun. 4, 2020

(30) Foreign Application Priority Data
Dec. 4, 2018   (TW) .............................. 107143497 A

(51) Int. Cl.
| | | |
|---|---|---|
| *C07C 67/303* | (2006.01) | |
| *B01J 23/46* | (2006.01) | |
| *B01J 21/04* | (2006.01) | |
| *B01J 8/10* | (2006.01) | |
| *B01J 8/08* | (2006.01) | |

(52) U.S. Cl.
CPC ............. *C07C 67/303* (2013.01); *B01J 8/085* (2013.01); *B01J 8/087* (2013.01); *B01J 8/10* (2013.01); *B01J 21/04* (2013.01); *B01J 23/462* (2013.01); *B01J 2208/0015* (2013.01); *B01J 2208/00141* (2013.01); *B01J 2208/00867* (2013.01)

(58) Field of Classification Search
CPC ... B01J 23/462; B01J 21/04; B01J 8/10; B01J 8/087; B01J 8/085; B01J 2208/00867; B01J 2208/0015; B01J 2208/00141
USPC ......................................................... 560/127
See application file for complete search history.

(56) References Cited

U.S. PATENT DOCUMENTS

| | | |
|---|---|---|
| 9,084,983 B2 | 7/2015 | Mirk |
| 2013/0053492 A1 | 2/2013 | Yoon et al. |
| 2016/0280629 A1 | 9/2016 | Jung et al. |

FOREIGN PATENT DOCUMENTS

CN            103130648 A       6/2013

*Primary Examiner* — Deborah D Carr
(74) *Attorney, Agent, or Firm* — Li & Cai Intellectual Property (USA) Office

(57) ABSTRACT

A hydrogenation method for increasing the yield of cyclohexane-1,4-dicarboxylic acid diisooctyl ester is provided. The hydrogenation method uses a hydrogenating reaction tank, which is equipped with a hollow-shaft gas-introducing mixer having air-extracting, air-exhausting and mixing functions, to allow hydrogen gas to be uniformly dispersed in a reaction solution. A ruthenium-on-alumina (Ru/Al$_2$O$_3$) hydrogenation catalyst can be used for carrying out a hydrogenation reaction under gentle conditions. Therefore, the hydrogenation catalyst can be used in a reduced amount, the risk of side reaction(s) can be reduced, and the yield of cyclohexane-1,4-dicarboxylic acid diisooctyl ester can reach at least 99% with a cis isomer proportion of at least 85.0%. The hydrogenation method shows extremely high economic benefit.

9 Claims, 2 Drawing Sheets

HYDROGENATION METHOD FOR INCREASING YIELD OF CYCLOHEXANE-1,4-DICARBOXYLIC ACID DIISOOCTYL ESTER

CROSS-REFERENCE TO RELATED PATENT APPLICATION

This application claims the benefit of priority to Taiwan Patent Application No. 107143497, filed on Dec. 4, 2018. The entire content of the above identified application is incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to a hydrogenation method for increasing the yield of cyclohexane-1,4-dicarboxylic acid diisooctyl ester, and more particularly to a method for preparing cyclohexane-1,4-dicarboxylic acid diisooctyl ester in a yield of at least 99.0% with a cis isomer proportion of at least 85.0%.

BACKGROUND OF THE DISCLOSURE

Phthalate based compounds have low plasticity coefficient, good processability and exceptional oil bleed property and are widely used as plasticizers for polyvinyl chloride (PVC). However, use of the phthalate based compounds is harmful to the human body and the environment, and has been prohibited for many years. Hydrogenation type terephthalat based compounds, in which benzene rings can be hydrogenated to produce cyclohexane), are used in place of the phthalate based compounds. Although the terephthalat based compounds are not listed as a controlled substance, the effects conveyed by their benzene structures should still be guarded against.

The preparation of hydrogenation type terephthalats relates to the hydrogenation of benzene rings, and catalysts capable of providing catalysis of benzene rings can theoretically be used therefor. Catalysts with different active compositions and/or carriers may achieve different hydrogenation efficiencies. At room temperature, the viscosity of terephthalate is about two times of that of phthalate. An important thing for promoting the hydrogenation reaction is to uniformly disperse hydrogen gas in a reaction solution of terephthalate. Generally, an increase of the hydrogenation reaction pressure may increase the solubility of hydrogen in liquids, and an increase of the reaction temperature may increase the reaction efficiency of the catalyst. However, the use of excessive reaction pressures may increase associated investment costs and negatively affect the safety of production. In addition, higher temperatures tend to cause side reactions, including the breakage of long carbon chains and the decomposition or reduction of ester groups. Although solvents may be added to reduce the viscosity of the reaction solution, the use of the solvents may reduce the production speed and increase the investment costs and require an additional separating process. In addition, it is difficult to control the contents of the cis and trans isomers in a product resulting from hydrogenation, and to produce cis-cyclohexane-1,4-dicarboxylic acid diisooctyl ester with a yield greater than 80%.

U.S. Patent Publication No. 2016/0280629 discloses the effect of the reactant viscosity on the hydrogenation efficiency. A multi-tubular reactor is used with a Ru hydrogenation catalyst to hydrogenate dioctyl terephthalate in a reaction solution at a high pressure of 150 bar, and an alcohol having at least two carbon atoms at 150 serving as a solvent is used to reduce the viscosity of the reaction solution. U.S. Pat. No. 9,084,983 discloses that a hydrogenation reaction for 0.34 wt % of dioctyl terephthalate is carried out for 12 hours by a 300 mL high-pressure batch reactor at 200 bar and 120° C. and in the presence of a $Ru/SiO_2$ hydrogenation catalyst having a $Ru/SiO_2$ ratio of 150 g/7.5 g. The resulting selection rate of cyclohexane-1,4-dicarboxylic acid diisooctyl ester is 97.7% with a conversion rate of 100%. China Patent No. 103130648 discloses hydrogenating dioctyl terephthalate at a high pressure of 12.9 MPa and high temperature of 200° C. It can be observed from the aforementioned prior arts that the hydrogenation reactions for dioctyl terephthalate all require a high pressure of least 100 bar, and this may cause an increase in costs. The aforementioned prior arts disclose that the yields of cyclohexane-1,4-dicarboxylic acid diisooctyl ester are about 97.7%, but do not disclose the proportion of the cis structure. In addition, U.S. Patent Publication No. 2013/0053492 discloses using a transesterification reaction to synthesize cyclohexane-1,4-dicarboxylic acid (C4-C20) alkyl ester having excellent plasticizing properties for PVC resin.

In the hydrogenation reaction of benzene rings, rhodium (Rh) metal has better properties than ruthenium (Ru) and palladium (Pd) metals, but is more expensive. In consideration of economic benefits, Ru catalysts have been widely studied in relevant literatures. In the literatures, a high pressure above 100 bar is required to increase the hydrogenation reactivity of Ru catalysts for terephthalate. In addition, solvents may be added to increase the solubility of hydrogen so as to increase the hydrogenation efficiency. However, this may cause an increase in costs.

SUMMARY OF THE DISCLOSURE

The present disclosure provides a hydrogenation method for increasing the yield of cyclohexane-1,4-dicarboxylic acid diisooctyl ester. The features of the present disclosure that have been explored in-depth by the inventors are as follows: (1) a cost-competitive ruthenium metal catalyst is used together with an alumina carrier to form a single metal ruthenium-on-alumina ($Ru/Al_2O_3$) hydrogenation catalyst that has high activity for hydrogenation of benzene rings; (2) a reaction tank uses a gas-directing mixer having a magnetic fluid feedthrough, which has air-extracting, air-exhausting and mixing functions. The yield of cyclohexane-1,4-dicarboxylic acid diisooctyl ester can reach at least 99% with a cis isomer proportion of at least 85.0% by processing equipment and operating conditions, which has economic and investment benefits, in the presence of the ruthenium-on-alumina ($Ru/Al_2O_3$) hydrogenation catalyst.

The hydrogenation method for increasing the yield of cyclohexane-1,4-dicarboxylic acid diisooctyl (2-ethylhexyl) ester of the present disclosure includes the following steps.

Step (1) is placing a reaction solution into a pressure-resistant hydrogenating reaction tank provided with a hollow-shaft gas-introducing mixer. The reaction solution includes 80-100 wt % of dioctyl terephthalate (DOPO), and no solvents or thinners are added to the reaction solution.

Step (2) is adding a ruthenium-on-alumina hydrogenation catalyst to the reaction solution. The ruthenium-on-alumina catalyst is added in an amount of 0.01-15 wt % of the amount of dioctyl terephthalate.

Step (3) is feeding hydrogen gas into the hydrogenating reaction tank to maintain a hydrogen gas pressure at a constant value of 20-98 bar.

Step (4) is activating the hollow-shaft gas-introducing mixer of the hydrogenating reaction tank to mix the reaction solution at room temperature and the constant hydrogen gas pressure and raising the reaction solution to 120-150° C. for carrying out a hydrogenation reaction for 4-15 hours.

Step (5) is cooling the reaction solution to room temperature and removing the ruthenium-on-alumina catalyst after the completion of the hydrogenation reaction, so as to obtain a reaction product for composition analysis.

It is observed that when the hydrogenating reaction tank, which is provided with the hollow-shaft gas-introducing mixer having air-extracting, air-exhausting and mixing functions, is used for the hydrogenation of dioctyl terephthalate in the presence of the ruthenium-on-alumina ($Ru/Al_2O_3$) hydrogenation catalyst having activity, the contact efficiency between hydrogen gas and the reaction solution can be increased and thus the mass transfer resistance between hydrogen gas and the reaction solution can be reduced. Accordingly, the reaction solution of the hydrogenation reaction has a high enough concentration of dissolved hydrogen gas such that the hydrogenation catalyst can sufficiently act to result in a fast hydrogenation rate. Therefore, a high conversion rate can be achieved in a relatively short period of time even at a low temperature and the heat history can be reduced, such that a higher ratio of cis to trans structures in cyclohexane-1,4-dicarboxylic acid diisooctyl ester can be achieved.

Dioctyl terephthalate used in the hydrogenation reaction is produced by an esterification reaction between terephthalic acid (PTA) and isooctanol (2EH). Dioctyl terephthalate and the hydrogenation catalyst can be used to form a heterogeneous organic solution in the presence or absence of a solvent. The content of the reaction solution is 40-100 wt %, and preferably 80-100 wt %. The hydrogenation catalyst is added in an amount of 0.01-3.0 wt % of the amount of dioctyl terephthalate, and preferably 0.02-2.0 wt %. If the amount of the hydrogenation catalyst is less than 0 01 wt %, the hydrogenation reaction cannot be carried out efficiently. However, the reaction rate and yield do not increase proportionally with the increase in the amount of the hydrogenation catalyst. It would be uneconomical if the amount of the hydrogenation catalyst is greater than 3.0 wt %. Before raising the temperature, the hydrogen gas pressure is increased to and maintained at less than 20 bar at room temperature, and the reaction solution is mixed at 1500 rpm for at least 10 minutes. The hydrogenation reaction temperature is 60-200° C., and preferably 120-150° C. The reaction process uses hydrogen gas to maintain a pressure of 10-200 bar, and preferably 20-98 bar, such that the reacting ingredients are present in in the reaction solution. The hydrogenation reaction time is 0.5-20 hours, and preferably 4-15 hours. The hydrogenation reaction product includes the unreacted dioctyl terephthalate, the solvent, impurity(ies) resulting from hydrogenolysis, the hydrogenation catalyst and its derivatives, and etc. In the hydrogenation reaction product, the unreacted dioctyl terephthalate is present in an amount of 0-1 wt %, cyclohexane-1,4-dicarboxylic acid diisooctyl ester is present in an amount of 80-100 wt %, the solvent is present in an amount of 0-20 wt %, the hydrogenation catalyst is present in an amount of 0.02-2 wt %, and the impurity(ies) is (are) present in an amount of 0-5 wt %.

The term "a reaction tank provided with a hollow-shaft gas-directing mixer having air-extracting, air-exhausting and mixing functions" as used in the present disclosure includes a pressure-resistant vessel having a rotary mixing device (also called "hollow-shaft gas-directing mixer") that is capable of mixing and promoting gas-liquid contact. The rotary mixing device capable of mixing and promoting gas-liquid contact has air-extracting and air-exhausting capabilities. The mixing device includes a hollow rotating shaft, which has an upper part with an air inlet hole and a lower part with an air outlet hole, and an impeller disposed on the lower part and corresponding in position to the air outlet hole. The hollow rotating shaft of the mixing device can be further equipped with an additional mixer that includes a blade and a baffle plate, so as to promote the liquid circulation in the reaction tank and prevent bubbles from prematurely disappearing while the bubbles bond to each other. The reaction tank provided with the hollow-shaft gas-directing mixer can additionally have a board-type heat exchanger or a coil pipe equipped therein to facilitate heat removal from the hydrogenation reaction so as to increase the hydrogenation reaction rate. In addition, the operation of the hollow-shaft gas-directing mixer for hydrogenating dioctyl terephthalate can be a batch operation, a semi-batch operation or a continuous operation.

When the hollow-shaft gas-directing mixer disposed in the reaction tank that is used for hydrogenating dioctyl terephthalate is in operation, hydrogen gas above the liquid surface of the reaction solution can be extracted into a gas channel inside the hollow-shaft gas-directing mixer via the air inlet hole, and subsequently be discharged to and uniformly dispersed in the reaction solution via the air outlet hole and the impeller. Accordingly, the contact efficiency between hydrogen gas and the reaction solution can be increased.

The reaction tank used in the present disclosure is a pressure-resistant airtight vessel that has a concave bottom surface in a hemispherical or elliptical shape or a conical bottom surface. A cover used for the vessel is not within the scope of the present disclosure, and can be connected to the vessel by a flange or welding. In order to provide a suitable liquid mixing function and effective air-extracting and air-exhausting functions, the vessel preferably has a height to diameter ratio between 0.4 and 3.

The concept of the hollow-shaft gas-directing mixer is described as follows, together with the figures of the present disclosure. FIG. 1 and FIG. 2 are side and top views showing the hollow-shaft gas-directing mixer having the aforesaid features.

The hollow-shaft gas-directing mixer as shown in FIG. 1 and FIG. 2 includes a hollow rotating shaft 32 that has a gas channel 34 therein for delivering hydrogen gas. The hollow rotating shaft 32 has an air inlet hole 35 at an upper part thereof, an air outlet hole 36 at a lower part thereof, and an impeller 37 disposed on the lower part and corresponding in position to the air outlet hole 36. The impeller 37 includes a number of blades 33 that are fixed in position by upper and lower discs 38. The blades 33 can be flat, curved or concave in shape. In addition, the hollow rotating shaft 32 can be driven by a motor in a mechanical or electromagnetic manner.

The present disclosure, considering the following two points, provides the hydrogenation method for increasing the yield of cyclohexane-1,4-dicarboxylic acid diisooctyl ester. Firstly, a cost-competitive ruthenium metal catalyst is used together with an alumina carrier to form a hydrogenation catalyst that has high activity and good reusability. Generally, the increase of the amount of the hydrogenation catalyst has a positive relation with the conversion and selection rates of the hydrogenating of benzene rings. For industrialization, it is necessary to provide a balance between product quality and manufacturing costs. Therefore, the reduction of the reaction time cannot merely depend on the increase in the amount of the hydrogenation catalyst.

Secondly, a mixer having a magnetic shaft seal, which has air-extracting, air-exhausting and mixing functions, can produce a pressure difference when rotating to introduce hydrogen gas above the reaction solution into the gas channel of the hollow rotating shaft via the air inlet hole and deliver the introduced hydrogen gas to the reaction solution via the air outlet hole in the presence of the hydrogenation catalyst. Accordingly, the contact efficiency between hydrogen gas and the reaction solution can be increased and thus the reaction solution of the hydrogenation reaction has a high enough concentration of dissolved hydrogen gas, such that the mass transfer resistance between hydrogen gas and the reaction solution can be reduced to achieve an ideal mixing effect. Therefore, the determination in the rate determining step of the hydrogenation reaction can be determined by the surface reaction of the hydrogenation catalyst, such that the hydrogenation catalyst can be fully utilized and be used in a reduced amount and a high conversion rate of cyclohexane-1,4-dicarboxylic acid diisooctyl ester can be achieved without operating at excessively high pressure.

Based on the above two points, the hydrogenation reaction can be carried out at a relatively low temperature of 100-150° C., preferably 120-135° C. so as to reduce side reactions and heat history. Therefore, cyclohexane-1,4-dicarboxylic acid diisooctyl ester resulting from the hydrogenation reaction has a higher ratio of cis to trans structures.

The hydrogenation method of the present disclosure uses the ruthenium-on-alumina ($Ru/Al_2O_3$) hydrogenation catalyst for the production of cyclohexane-1,4-dicarboxylic acid diisooctyl ester, such that the operating pressure can be reduced as much as possible and the yield of cyclohexane-1,4-dicarboxylic acid diisooctyl ester can reach at least 99% with a cis isomer proportion of at least 85.0%.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The present disclosure will become more fully understood from the following detailed description and accompanying drawings.

DETAILED DESCRIPTION OF THE EXEMPLARY EMBODIMENTS

Figure 1:
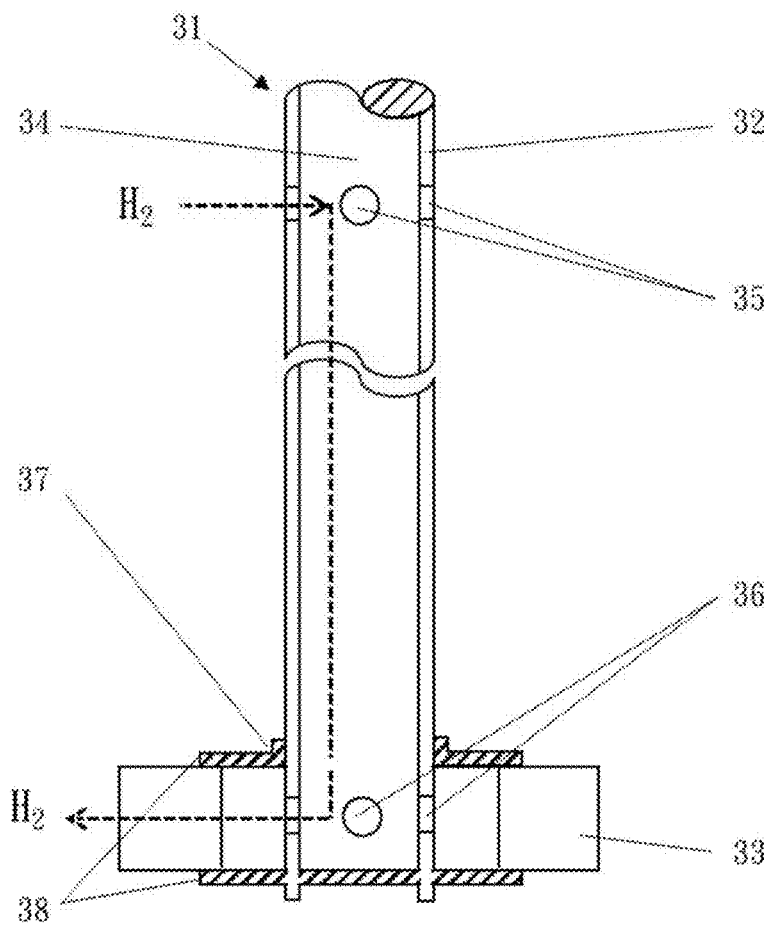
FIG. 1 is a side view of a hollow rotating shaft of a gas-introducing mixer having air-extracting, air-exhausting and mixing functions.
Figure 2:
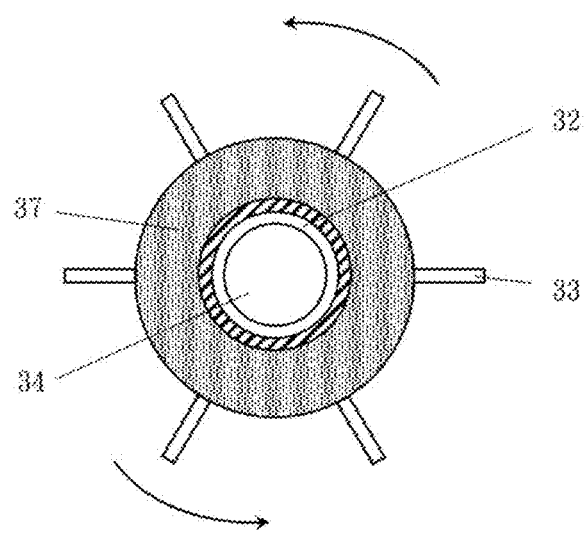
FIG. 2 is a top view of the hollow rotating shaft of the gas-introducing mixer having the air-extracting, air-exhausting and mixing functions.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

Examples 1-5 and Comparative Examples 1-4 are used to more specifically illustrate the present disclosure without limiting the scope of the present disclosure.

The conversion rate, selection rate, yield and cis-trans ratio are calculated as follows:

Conversion rate (%)=(GC integral area of dioctyl terephthalate before reaction−GC integral area of dioctyl terephthalate after reaction)/GC integral area of dioctyl terephthalate before reaction×100%

Selection rate (%)=GC integral area of cyclohexane-1,4-dicarboxylic acid diisooctyl ester after reaction/(GC integral area of dioctyl terephthalate before reaction−GC integral area of dioctyl terephthalate after reaction)×100%

Yield (%)=GC integral area of cyclohexane-1,4-dicarboxylic acid diisooctyl ester after reaction/GC integral area of dioctyl terephthalate before reaction×100%

Cis isomer proportion (%) of cyclohexane-1,4-dicarboxylic acid diisooctyl ester=GC integral area of cis isomer after reaction/GC integral area of cyclohexane-1,4-dicarboxylic acid diisooctyl ester×100%

EXAMPLE 1

Figure 3:
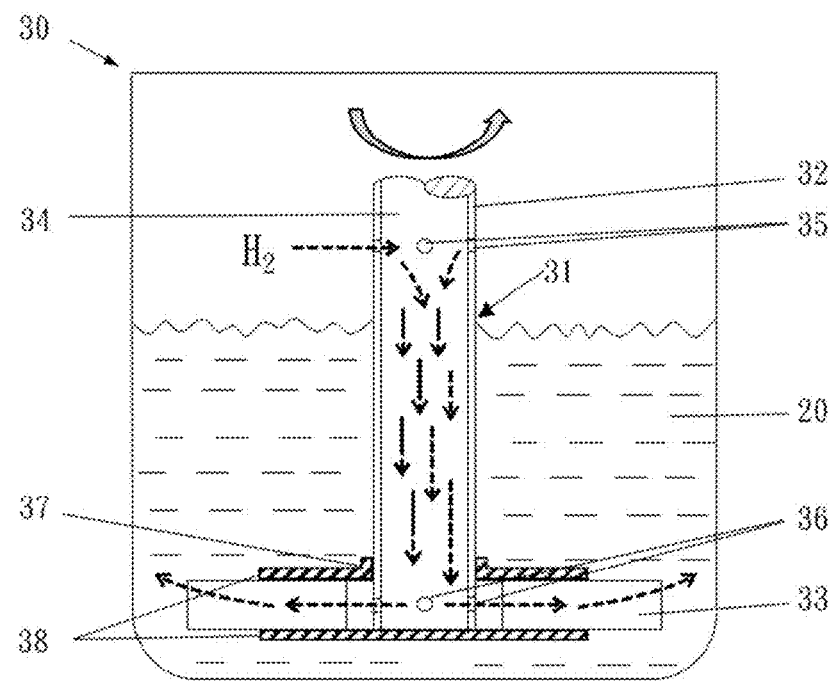
FIG. 3 is a schematic view showing a reaction tank equipped with the gas-introducing mixer having the air-extracting, air-exhausting and mixing functions.

A reaction solution containing 250 g of dioctyl terephthalate was placed into a 450 mL pressure-resistant reaction tank equipped with a hollow-shaft gas-introducing mixer as shown in FIG. 3. Next, 1.6 g of a ruthenium-on-alumina (Ru/Al$_2$O$_3$) hydrogenation catalyst was added to the reaction solution and hydrogen gas was continuously fed into the reaction tank to maintain a hydrogen gas pressure of 98 bar. Next, a mixing motor of the reaction tank was activated to have a rotation speed of 1400 rpm, and a temperature within the reaction tank was maintained at room temperature for 10 minutes and subsequently raised to 120° C. for carrying out a hydrogenation reaction. The travel time between the rise of the temperature and the end of the hydrogenation reaction is about 4 hours. After completion of the hydrogenation reaction, the reaction solution was cooled to room temperature and the hydrogenation catalyst was removed by filtration, so as to obtain a reaction product for combination analysis. The analysis results are shown in Table 1. The amount of the hydrogenation catalyst is 1 wt %, and the resulting yield of cyclohexane-1,4-dicarboxylic acid diisooctyl ester is 99% with a cis isomer proportion of 86.7%.

EXAMPLE 2

The ruthenium-on-alumina catalyst is the same as that used in Example 1. All conditions are the same as those used in Example 1, except that the hydrogen gas pressure in the reaction tank is lowered to 20 bar from 98 bar, the amount of the hydrogenation catalyst is lowered to 0.7 wt % from 1 wt %, and the hydrogenation reaction time is about 4 hours. The resulting yield of cyclohexane-1,4-dicarboxylic acid diisooctyl ester is 99.0% with a cis isomer proportion of 86.1%.

EXAMPLE 3

The ruthenium-on-alumina catalyst is the same as that used in Example 2. All conditions are the same as those used in Example 2, except that the amount of the hydrogenation catalyst is lowered to 0.52 wt % and the hydrogenation reaction time is about 5 hours. The resulting yield of cyclohexane-1,4-dicarboxylic acid diisooctyl ester is 99.0% with a cis isomer proportion of 86.8%.

EXAMPLE 4

The ruthenium-on-alumina catalyst is the same as that used in Example 2. All conditions are the same as those used in Example 2, except that the amount of the hydrogenation catalyst is lowered to 0.45 wt % and the hydrogenation reaction time is about 5 hours. The resulting yield of cyclohexane-1,4-dicarboxylic acid diisooctyl ester is 99.1% with a cis isomer proportion of 86.8%.

EXAMPLE 5

The ruthenium-on-alumina catalyst is the same as that used in Example 2. All conditions are the same as those used in Example 2, except that the amount of the hydrogenation catalyst is lowered to 0.2 wt % and the hydrogenation reaction time is about 5 hours. The resulting yield of cyclohexane-1,4-dicarboxylic acid diisooctyl ester is 99.1% with a cis isomer proportion of 86.4%.

EXAMPLE 6

The ruthenium-on-alumina catalyst is the same as that used in Example 3. All conditions are the same as those used in Example 3, except that the amount of the hydrogenation catalyst is lowered to 0.06 wt %, the hydrogenation temperature is 120-130° C., and the reaction time is about 10 hours. The resulting yield of cyclohexane-1,4-dicarboxylic acid diisooctyl ester is 99.1% with a cis isomer proportion of 86.7%.

COMPARATIVE EXAMPLE 1

A ruthenium-on-carbon (Ru/C) catalyst is used as the hydrogenation catalyst. The hydrogen gas pressure is 20 bar. The reaction temperature is 135° C. The hydrogenation catalyst is added in an amount less than 1 wt %. The hydrogenation time is 9 hours. The resulting yield of cyclohexane-1,4-dicarboxylic acid diisooctyl ester is 95.2% with a cis isomer proportion of 79.4%.

COMPARATIVE EXAMPLE 2

Figure 4:
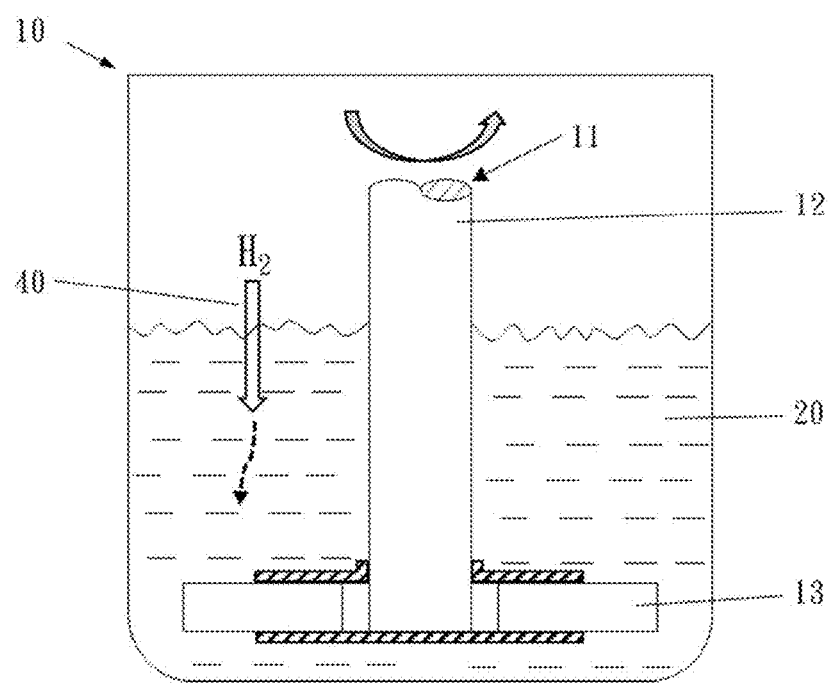
FIG. 4 is a schematic view of a conventional hydrogenation tank.

All conditions are the same as those used in Example 5, except that a conventional impeller mixer which does not have air-extracting and air-exhausting functions is used for hydrogenation reaction, a hydrogen gas spraying component is additionally equipped to direct hydrogen gas into the reaction tank from a position below a liquid surface, and the amount of the hydrogenation catalyst is increased by 7.5 times. As shown in FIG. 4, a conventional hydrogenating reaction tank 10 is equipped with an impeller mixer 11, in which a rotating shaft 12 is used to drive a blade 12 disposed at a terminal end of the rotating shaft 12 so as to mix a reaction solution 20. A hydrogen gas spraying component 40 can be placed into the reaction solution 20 to introduce and force a high-pressure hydrogen gas to contact the reaction solution 20. In a test that the hydrogenation catalyst is added in an amount less than 1.5 wt % and the hydrogenation time is about 5 hours, the resulting yield of cyclohexane-1,4-dicarboxylic acid diisooctyl ester is 98.7% with a cis isomer proportion of 83.3%.

COMPARATIVE EXAMPLE 3

All conditions are the same as those used in Comparative Example 1, except that a conventional impeller mixer which does not have air-extracting and air-exhausting functions is used for hydrogenation reaction and the amount of the hydrogenation catalyst is increased by 25%. The hydrogenation time is 15 hours, and the resulting yield of cyclohexane-1,4-dicarboxylic acid diisooctyl ester is 94.8% with a cis isomer proportion of 75.5%.

COMPARATIVE EXAMPLE 4

The ruthenium-on-carbon catalyst is the same as that used in Comparative Example 3. The amount of the hydrogenation catalyst is increased by 1.5 wt %. The hydrogen gas pressure is raised to 50 bar. The reaction temperature is raised to 150° C. The hydrogenation time is 10 hours. The conversion rate is 100%. The resulting yield of cyclohexane-1,4-dicarboxylic acid diisooctyl ester is 94.9% with a cis isomer proportion of 77.6%.

TABLE 1

| Hydrogenating reaction tank | Examples | | | | | |
|---|---|---|---|---|---|---|
| | 1 | 2 | 3 | 4 | 5 | 6 |
| | Equipped with gas-introducing mixer | | | | | |
| Hydrogenation catalyst | 5% Ru/Al$_2$O$_3$ | | | | | |
| Dioctyl terephthalate (g) | 250 | 250 | 250 | 250 | 250 | 250 |
| 2EH (g) | 0 | 0 | 0 | 0 | 0 | 0 |
| Amount of hydrogenation catalyst (wt %) | 1 | 0.7 | 0.52 | 0.45 | 0.2 | 0.06 |
| Hydrogen gas pressure (bar) | 98 | 20 | 20 | 20 | 20 | 20 |
| Reaction temperature (° C.) | 120 | 120 | 120 | 120 | 120 | 120-130 |
| Reaction time (hours) | 4 | 4 | 5 | 5 | 5 | 10 |
| Conversion rate (%) | 100 | 100 | 100 | 100 | 99.9 | 100 |
| Selection rate (%) | 99.0 | 99.0 | 99.0 | 99.1 | 99.1 | 99.1 |
| Yield of cyclohexane-1,4-dicarboxylic acid diisooctyl ester (%) | 99.0 | 99.0 | 99.0 | 99.1 | 98.9 | 99.1 |
| Cis isomer proportion (%) | 86.7 | 86.1 | 86.8 | 87.0 | 86.4 | 86.7 |

TABLE 2

| Hydrogenating reaction tank | Comparative Examples | | | |
|---|---|---|---|---|
| | 1 | 2 | 3 | 4 |
| | Equipped with gas-introducing mixer | | Equipped with impeller mixer | |
| Hydrogenation catalyst | 5% Ru/C | 5% RU/Al$_2$O$_3$ | 5% Ru/C | 5% Ru/C |
| Dioctyl terephthalate (g) | 250 | 250 | 250 | 250 |
| 2EH (g) | 0 | 0 | 0 | 0 |
| Amount of hydrogenation catalyst (wt %) | 1 | 1.5 | 1.25 | 1.5 |
| Hydrogen gas pressure (bar) | 20 | 20 | 20 | 50 |
| Reaction temperature (° C.) | 135 | 120 | 135 | 150 |
| Reaction time (hours) | 9 | 5 | 15 | 10 |
| Conversion rate (%) | 100 | 100 | 100 | 100 |
| Selection rate (%) | 95.2 | 98.7 | 94.8 | 94.9 |
| Yield of cyclohexane-1,4-dicarboxylic acid diisooctyl ester (%) | 95.2 | 98.7 | 94.8 | 94.9 |
| Cis isomer proportion (%) | 79.4 | 83.3 | 75.5 | 77.6 |

[Result]

1. It is observed from the comparison between Example 1 and Example 2 that the conversion rate of cyclohexane-1,4-dicarboxylic acid diisooctyl ester can reach 100% with 4 hours when the hydrogenation pressure is lowered to 20 bar from 98 bar and the amount of the catalyst is reduced by 30%. The resulting yield of cyclohexane-1,4-dicarboxylic acid diisooctyl ester is at least 99.0% with a cis isomer proportion of at least 85.0%. Also, it is shown that the hydrogenating reaction tank, which uses a gas-introducing mixer having air-extracting, air-exhausting and mixing functions, can increase the mass transfer efficiency of hydrogen gas in the reaction solution and significantly reduce the hydrogenation pressure.

2. It is observed from the comparison between Example 2 and Examples 3-5 that even when the amount of the hydrogenation catalyst is reduced to 0.2 wt % from 0.7 wt %, the yield of cyclohexane-1,4-dicarboxylic acid diisooctyl ester can still reach at least 99.0% with a cis isomer proportion of at least 85.0% within 4-5 hours. Also, it is shown that the hydrogenating reaction tank, which uses a gas-introducing mixer having air-extracting, air-exhausting and mixing functions, can increase the contact efficiency between hydrogen gas and the reaction solution, such that the reaction solution of the hydrogenation reaction has a high enough concentration of dissolved hydrogen gas. Accordingly, the hydrogenation catalyst can have an extremely high activity and result in a fast hydrogenation rate, and the amount of the hydrogenation catalyst can be reduced.

3. It is observed from the comparison between Example 2 and Comparative Example 1 that, in the presence of the Ru/C catalyst, even when the amount of the hydrogenation catalyst and the hydrogenation temperature are increased, there is still a need for a hydrogenation reaction time of 9 hours. The resulting yield of cyclohexane-1,4-dicarboxylic acid diisooctyl ester is 95.2% with a cis isomer proportion of 79.4%. It is shown that the Ru/Al$_2$O$_3$ catalyst is a preferable catalyst for the hydrogenation reaction of dioctyl terephthalate.

4. It is observed from the comparison between Example 5 and Comparative Example 2 that, compared to the conventional hydrogenation reactor, the reactor equipped with the hollow-shaft gas-introducing mixer can produce a higher yield (99.0%) of cyclohexane-1,4-dicarboxylic acid diisooctyl ester and a higher cis/trans ratio (86.4%) under the same reaction conditions such as hydrogenation catalyst (Ru/Al$_2$O$_3$), pressure, temperature, and hydrogenation time (e.g., 5 hours), and the hydrogenation catalyst can be added in an amount 1/7.5 times lower.

5. The hydrogenation catalyst used in Example 6 is a recycled ruthenium-on-alumina (Ru/Al$_2$O$_3$) catalyst that was used in Example 3 about 10 times. The resulting yield of cyclohexane-1,4-dicarboxylic acid diisooctyl ester and cis/trans ratio are still high while the reaction time is increased to 10 hours and the reaction temperature is 120-130° C. It is shown that the hydrogenation catalyst still has good activity.

6. It is observed from the comparison between Comparative Example 1 and Comparative Example 3 that the reactor equipped with the hollow-shaft gas-introducing mixer can achieve a conversion rate of 100% under the same hydrogenation catalyst (Ru/C), pressure and temperature while the amount of the hydrogenation catalyst is reduced by 25% and the hydrogenation reaction time is reduced to 9 hours from 15 hours. The resulting yield of cyclohexane-1,4-dicarboxylic acid diisooctyl ester is still high and the cis/trans ratio is increased to 79.4% from 75.5%. It is observed that the cis/trans ratio can be affected by the reaction time. If the reaction time is too long, the thermodynamic would trend toward the generation of the trans structure. Therefore, a short reaction time is required for obtaining a high conversion. The reactor equipped with the hollow-shaft gas-introducing mixer having air-extracting, air-exhausting and mixing functions can economically produce cyclohexane-1,4-dicarboxylic acid diisooctyl ester with a cis/trans ratio greater than 85% in the presence of the Ru/Al$_2$O$_3$ catalyst having high hydrogenation activity.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A hydrogenation method for increasing the yield of cyclohexane-1,4-dicarboxylic acid diisooctyl ester, the yield being at least 99.0% with a cis isomer proportion of at least 85.0%, the hydrogenation method comprising:
   (1) placing a reaction solution into a hydrogenating reaction tank, the reaction solution including 80-100 wt % of dioctyl terephthalate, wherein the hydrogenating reaction tank is equipped with a hollow-shaft gas-introducing mixer having air-extracting, air-exhausting and mixing functions;
   (2) adding a ruthenium-on-alumina (Ru/Al$_2$O$_3$) hydrogenation catalyst to the reaction solution, the ruthenium-on-alumina hydrogenation catalyst added in an amount of 0.01-15 wt % of the amount of dioctyl terephthalate;
   (3) feeding hydrogen gas into the hydrogenating reaction tank to maintain a hydrogen gas pressure at a constant value of 20-98 bar;
   (4) activating the hollow-shaft gas-introducing mixer of the hydrogenating reaction tank to mix the reaction solution and carrying out a hydrogenation reaction at 120-150° C. for 4-15 hours; and
   (5) cooling the reaction solution to room temperature and removing the ruthenium-on-alumina hydrogenation catalyst after the completion of the hydrogenation reaction.

2. The hydrogenation method according to claim 1, wherein in the step (4), the reaction solution is maintained at room temperature and the hydrogen gas pressure of 20-98 bar for 10 minutes before raising the reaction temperature.

3. The hydrogenation method according to claim 1, wherein in the step (2), the amount of the ruthenium-on-alumina hydrogenation catalyst is 0.02-10 wt % of the amount of dioctyl terephthalate.

4. The hydrogenation method according to claim 1, wherein in the step (3), the hydrogen gas pressure in the hydrogenating reaction tank is maintained at 20 bar.

5. The hydrogenation method according to claim 1, wherein in the step (1), the content of dioctyl terephthalate in the reaction solution is 100 wt %.

6. The hydrogenation method according to claim 1, wherein in the step (4), the hydrogenation reaction is carried out for 4 hours.

7. The hydrogenation method according to claim 1, wherein in the step (4), the hydrogenation reaction is carried out at 120-130° C.

8. The hydrogenation method according to claim 1, wherein in the step (1), the hydrogenating reaction tank is cylindrical in shape and has a height to diameter ratio of 0.4 to 3.

9. The hydrogenation method according to claim 1, wherein in the step (1), the hydrogenating reaction tank is additionally equipped with a board-type heat exchanger or a coil pipe to immediately remove heat released from the hydrogenation reaction so as to avoid heat accumulation.

* * * * *